(12) United States Patent
Miyazawa

(10) Patent No.: US 7,375,644 B2
(45) Date of Patent: May 20, 2008

(54) FOOT SWITCH AND OUTPUT SYSTEM HAVING FOOT SWITCH

(75) Inventor: Taro Miyazawa, Tokyo (JP)

(73) Assignee: Olympus Corporation, Tokyo (JP)

( * ) Notice: Subject to any disclaimer, the term of this patent is extended or adjusted under 35 U.S.C. 154(b) by 134 days.

(21) Appl. No.: 11/218,253

(22) Filed: Sep. 1, 2005

(65) Prior Publication Data

US 2006/0047200 A1 Mar. 2, 2006

(30) Foreign Application Priority Data

Sep. 1, 2004 (JP) .............................. 2004-254403

(51) Int. Cl.
*G08B 21/00* (2006.01)

(52) U.S. Cl. .................. 340/636.1; 320/136; 320/134

(58) Field of Classification Search ............ 340/636.1; 324/426; 320/136, 132, 134; 606/34, 1; 429/90

See application file for complete search history.

(56) References Cited

U.S. PATENT DOCUMENTS

| | | | |
|---|---|---|---|
| 4,325,010 A * | 4/1982 | Lowndes ..................... 318/139 |
| 5,430,434 A | 7/1995 | Lederer et al. |
| 5,606,242 A * | 2/1997 | Hull et al. ................... 320/106 |
| 6,069,468 A * | 5/2000 | Sonobe ........................ 320/106 |
| 6,074,388 A * | 6/2000 | Tockweiler et al. ........... 606/34 |
| 6,148,408 A * | 11/2000 | Shimoda ..................... 713/320 |
| 6,157,169 A | 12/2000 | Lee |
| 6,383,183 B1 * | 5/2002 | Sekino et al. ................ 606/34 |
| 6,437,699 B1 | 8/2002 | Hayakawa |
| 6,449,726 B1 | 9/2002 | Smith |
| 6,563,766 B1 * | 5/2003 | Nakamiya ..................... 368/64 |
| 2004/0027249 A1 * | 2/2004 | Heiser et al. ............. 340/636.1 |
| 2004/0232884 A1 * | 11/2004 | Vaillancourt et al. ....... 320/132 |

FOREIGN PATENT DOCUMENTS

| | | |
|---|---|---|
| DE | 197 30 456 A1 | 1/1999 |
| DE | 102 35 956 A1 | 2/2004 |
| DE | 102 45 591 A1 | 4/2004 |
| EP | 0 891 745 B1 | 1/1999 |
| JP | 5-23347 | 2/1993 |

OTHER PUBLICATIONS

Abstract of International Publication No. WO 02/49509 A2, published Jun. 27, 2002.
Abstract of International Publication No. WO 2004/019751 A2, published Mar. 11, 2004.

* cited by examiner

*Primary Examiner*—Davetta W. Goins
*Assistant Examiner*—Hongmin Fan
(74) *Attorney, Agent, or Firm*—Scully, Scott, Murphy & Presser, P.C.

(57) ABSTRACT

The foot switch includes a pedal, an output command signal generating section for transmitting, when the pedal is operated, an output command signal to an apparatus which has a function of producing active output, a storage battery for supplying electrical power to the output command signal generating section, a condition-detecting section for detecting a remaining capacity of the storage battery, and a notifying section for making notification of an amount corresponding to the remaining capacity detected by the condition-detecting section. The condition-detecting section can detect the remaining capacity based on the remaining voltage of the storage battery.

13 Claims, 6 Drawing Sheets

FOOT SWITCH AND OUTPUT SYSTEM HAVING FOOT SWITCH

CROSS-REFERENCE TO RELATED APPLICATION

This application is related to Japanese Patent Application No. 2004-254403 filed on Sep. 1, 2004, the contents of which are hereby incorporated by reference.

BACKGROUND OF THE INVENTION

1. Technical Field

The present invention relates to a foot switch which transmits a signal for commanding generation of active output to an apparatus main body having a function of generating active output, and relates to an output system including such a foot switch and an apparatus main body.

2. Related Art

One example of such an output system is an ultrasonic surgical system disclosed in Japanese Unexamined Patent Application Publication No. 05-023347. An apparatus main body of this ultrasonic surgical system includes a main unit for generating drive signals (high frequency voltage signals). A handpiece having a probe at a tip thereof and gripped by the operator is electrically connected to the main unit through a cable. The handpiece includes therein an ultrasonic transducer which converts the drive signals into mechanical vibration (ultrasonic band signals). The ultrasonic vibration generated by the ultrasonic transducer is transmitted to the probe while being amplified. A water supply/suction path is provided in the handpiece and the probe. The system is so arranged that when the water supply/suction path is connected to a water supply/suction device, water supply/suction treatment can be effected through an opening formed at an end face of the probe and its vicinity.

More specifically, treatment can be performed by destroying and emulsifying tissues such as of liver parenchyma while performing perfusion through the opening formed in the ultrasonically vibrating probe, and by sucking/removing the debris together with the superfusate through the supply/suction path. An electric knife system may be used together with such an ultrasonic surgical system. Hemostatic treatment or the like can be effected by connecting the electric knife to the handpiece to make a high frequency output through the handpiece of the electric knife.

Since the treatment device including the handpiece or an electric knife is gripped by the operator during surgery, it is appropriate that on/off operation of the treatment device is performed through a foot switch except for a case where a pinpoint operation is particularly required (for example, when hemostatic treatment is performed by the electric knife). That is because, since depressing a switch for a long time with fingers to keep a treatment device in an on-state is a great burden to the operator, employing a foot switch which enables the operator to keep depressing the switch by the operator's weight is desirable from an ergonomical point of view.

It is to be noted that in order to enable selection from among different output types, for example, selection between water supply operation and suction operation, a plurality of pedals are generally disposed in a foot switch. A foot switch is required to have an excellent user-interface design so that the operator can readily distinguish the plurality of pedals.

A foot switch is typically electrically connected to an apparatus main body through a cable to transmit the operational statuses of the foot switch pedals to the apparatus main body through the cable. When using a plurality of different output systems in surgical operation (e.g., when using an ultrasonic surgical system and an electric knife system), a plurality of foot switches are used. The plurality of foot switches are placed close to the operator's feet, and used while there locations are permutated depending on the progress of the surgical operation. In such a case, however, the cables of the plurality of the foot switches sometimes tangle with each other, which significantly lowers the operator's convenience since appropriate locations of the foot switches cannot be ensured. Particularly, in advanced manipulation in which the operator often keeps moving around the operating table during a surgical operation, since the locations of the foot switches are required to be changed following the operator's movement even in a particular case, the chance of the occurrences of the cable tangling increases that much.

In order to prevent surgical operation from stopping due to such tangling of cables, it is known as described in U.S. Pat. No. 6,074,388, for example, to transfer the operational statuses of the pedals of a foot switch to an apparatus main body by means of radio communication. The foot switch in the surgical system described in the '388 patent incorporates a battery as a power source, and is arranged such that a warning is displayed in a display device at an appropriate time, so as to prevent interruption of a surgical operation by the low output voltage of the battery resulting from electrical discharge of the battery. The foot switch is also provided with an auxiliary battery.

In this surgical system, however, the operator cannot know how long the battery is able to supply power before the warning is displayed, and how long the battery is able to supply power after the warning is displayed. In other words, in this surgical system, it is not until when the warning is indicated that an operator is informed of the insufficiency of the remaining capacity of the battery, causing a problem of bad usability. In addition, since a foot switch of this surgical system incorporates an auxiliary battery, the size and weight of the foot switch become unavoidably large, and thus a problem of poor portability is also an issue.

SUMMARY OF THE INVENTION

The present invention provides a foot switch including:
a pedal;
an output command signal generating section transmitting, when the pedal is operated, an output command signal to an apparatus main body having a function of producing active output;
a storage battery supplying electrical power to the output command signal generating section;
a condition-detecting section detecting a remaining capacity of the storage battery; and
a notifying section making notification of an amount corresponding to the remaining capacity detected by the condition-detecting section.

The present invention also provides an output system including such a foot switch and an apparatus main body.

According to the present invention, it is possible to avoid a situation where a foot switch becomes unusable due to the low output voltage of its storage battery resulting from electrical discharge of the storage battery during surgery by checking, before conducting a surgical operation, the remaining usable time of the foot switch that can be estimated from the remaining capacity of the storage battery. Hence, according to the present invention, a small-sized and light weight foot switch excellent in portability can be provided, since it is unnecessary to provide the foot switch with an auxiliary battery.

The notification section for making a notification of an amount corresponding to the remaining capacity of a battery detected by a condition-detecting section may be provided in the apparatus main body.

DETAILED DESCRIPTION OF THE PREFERRED EMBODIMENTS

Figure 1A:
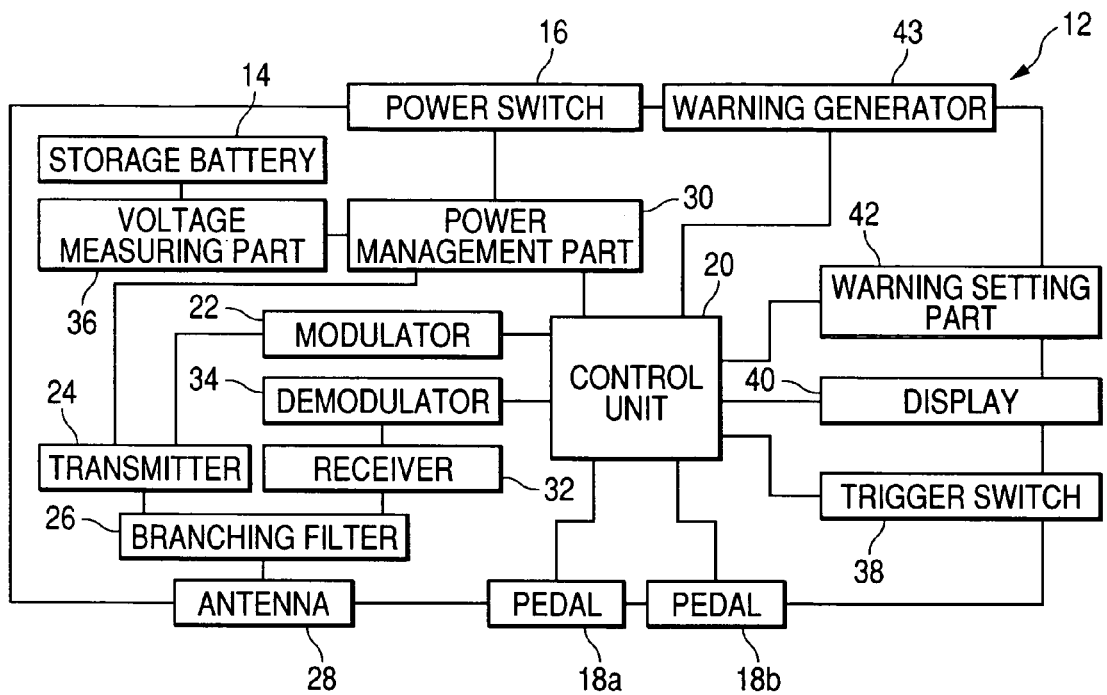
FIG. 1A is a block diagram showing a circuitry of a foot switch in an ultrasonic surgical system according to a first embodiment of the present invention.

Several ultrasonic surgical systems using a foot switch of the invention are described below as output systems. In the below described embodiments, identical reference characters are used for identical or corresponding parts.

An ultrasonic surgical system according to the first embodiment of the present invention is described below. This ultrasonic surgical system includes a foot switch 12 having the circuitry show in FIG. 1A and the appearance shown in FIG. 1B, and an apparatus main body 44 having the circuitry shown in FIG. 2A and the appearance shown in FIG. 2B.

The foot switch 12 is described first. As shown in FIG. 1A, the foot switch 12 is provided with a storage battery 14 serving as a power source, and is started up by the operation of a power switch 16 as an activation switch.

The foot switch 12 has a function of transmitting an output command signal (described later) to the apparatus main body 44. As shown in FIG. 1A, the foot switch 12 has a first pedal 18a and a second pedal 18b which are subjected to on/off operation. Each of the first and second pedals 18a, 18b, when switched on (closed), outputs an on-signal to a control unit 20. Upon reception of the on-signal, the control unit 20 generates an output command signal. The output command signal is transmitted to a transmitter 24, being modulated to an appropriate transmission code and transmission frequency by a modulator 22, and further transmitted to the apparatus main body 44 from an antenna 28 through a branching filter 26.

Electrical power is supplied to the transmitter 24 from the storage battery 14 through a power management part 30. The power management part 30 controls power to be supplied to the transmitter 24 to adjust transmission intensity of the modulated output command signal to an appropriate level. The control unit 20 may receive a radio signal, as required, transmitted from the apparatus main body 44 through the antenna 28, the branching filter 26, a receive 32 and a demodulator 34.

In this way, a communication section for transmitting and, if required, receiving a radio signal is constituted by the modulator 22, transmitter 24, branching filter 26, antenna 28, receiver 32 and demodulator 34. Also, an output command signal generating section for generating an output command signal, and transmitting an output command signal to the apparatus main body 44 is constituted by the control unit 20, the power management part 30 and the communication section.

The foot switch 12 also includes a trigger switch 38. As will be described hereunder, the foot switch 12 has a function of indicating remaining voltage every time the trigger switch 38 is operated. The function is described below.

A remaining voltage of the storage battery 14 corresponding to a remaining capacity of the storage battery 14 is measured by a voltage measuring part 36 serving as a condition-detecting section, which is disposed between the storage battery 14 and the power management part 30. When the trigger switch 38 is operated, the control unit 20 outputs a trigger signal to the power management part 30. Upon receipt of the trigger signal, the power management part 30 transmits the remaining voltage measured by the voltage measuring part 36 to the control unit 20. The control unit 20 then notifies a display 40, which serves as a notifying section, of the remaining voltage, by which the display 40 indicates the remaining voltage thereon. The control unit 20 controls the display 40 so that the remaining voltage is indicated for a predetermined period of time with the aid of a timer (not shown) capable of integrating the time of indication of the remaining voltage.

Further, the foot switch 12 is provided with a buzzer 43 serving as a warning generator. As will be described later, the foot switch 12 has a function of generating a warning in case a remaining usable time of the foot switch 12 becomes equal to or lower than a preset warning-generation time. In the present embodiment, the remaining time during which the storage battery 14 can supply power to the output command signal generating section, is considered to be the remaining usable time of the foot switch 12.

The relationship between the output voltage of the fully charged storage battery 14 and a capacity of the storage battery 14, i.e. a power suppliable time of the storage battery 14 is stored in advance in a memory (not shown) in the control unit 20. Upon completion of the charge of the storage battery 14, the power management part 30 measures the output voltage of the storage battery 14 with the aid of the voltage measuring part 36, and stores it in the memory in control unit 20. The control unit 20 can calculate a remaining power suppliable time corresponding to a remaining capacity of the storage battery 14 based on the remaining voltage of the storage battery 14 by referring to the output voltage and the relationship described above which are stored in the memory.

The foot switch 12 further comprises a warning setting part 42 for setting the warning-generation time. The warning setting part 42 outputs the warning-generation time that has been set by an operator, to the control unit 20. The control unit 20 then calculates a warning-generation-time voltage, which results from the addition of the remaining voltage of the storage battery 14 corresponding to the inputted warning-generation time, to a predetermined margin voltage. The control unit 20, when it has detected a remaining voltage of the storage battery 14 to be lower than the warning-generation-time voltage, permits the warning generator 43 to generate a warning.

Figure 1B:
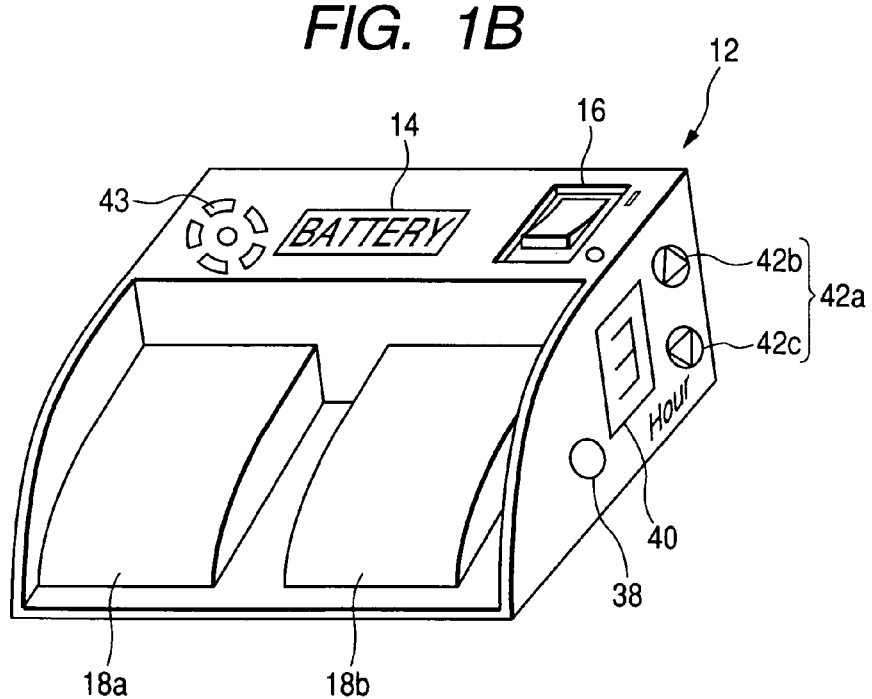
FIG. 1B is a perspective view showing an appearance of the foot switch of FIG. 1A.

As shown in FIG. 1B, the foot switch 12 is provided with the first and second pedals 18a, 18b which are depressed by an operator's foot, the antenna 28, the power switch 16 and the buzzer 43 serving as a warning generator.

The storage battery 14 is detachable from the foot switch 12. The storage battery 14 can be charged when it is attached to, and detached from the foot switch. When the storage battery 14 has been replaced by a new one, or when the storage battery 14 has been fully charged, the output voltage of the storage battery 14 is stored in the memory in the control unit 20. This output voltage is indicated on the display 40 for a predetermined period of time.

When the trigger switch 38 is manipulated, a remaining voltage is indicated on the display 40 for a predetermined period of time.

The foot switch 12 is also provided with a setting switch 42a. This setting switch 42a includes an UP-switch 42b and a DOWN-switch 42c which are juxtaposed in the vertical direction. By operating these UP-switch 42b and DOWN-switch 42c, a warning-generation time can be set. A warning-generation time set through the setting switch 42a is indicated on the display 40 for a predetermined period of time.

Figure 2A:
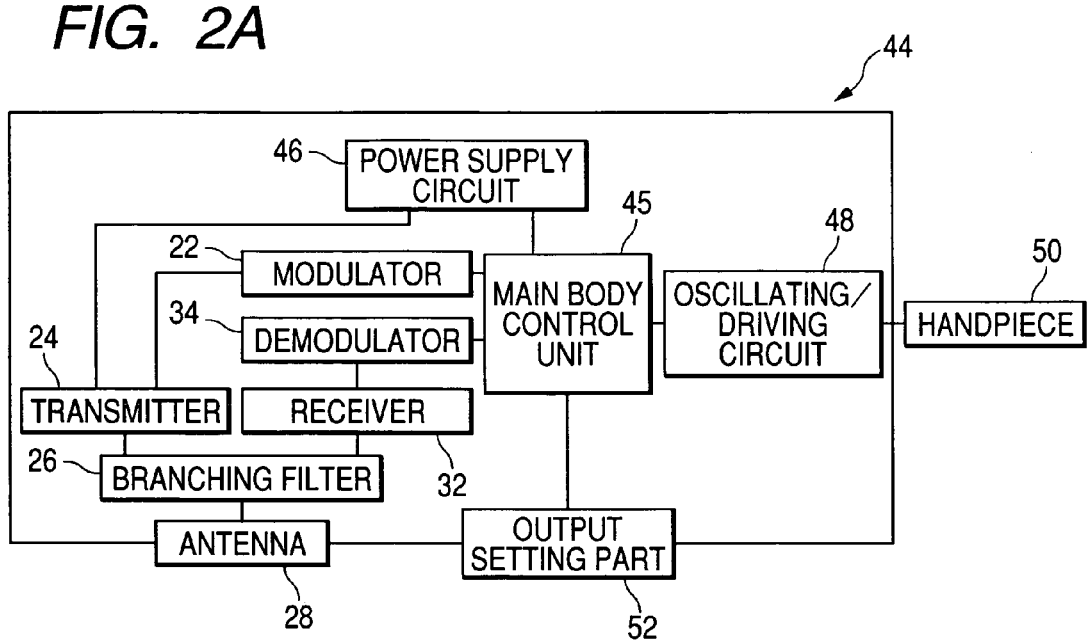
FIG. 2A is a block diagram showing a circuitry of an apparatus main body in the ultrasonic surgical system according to the first embodiment of the present invention.

The apparatus main body 44 is described hereunder. As shown in FIG. 2A, the modulated output command signal transmitted from the foot switch 12, as described above, is received by the receiver 32 through the antenna 28 and the branching filter 26. The output command signal is demodulated by the demodulator 34 and transmitted to a main body control unit 45. The main body control unit 45 may transmit a radio signal to the foot switch 12, as required, through the modulator 22, transmitter 24, branching filter 26 and antenna 28. In this case, the transmission intensity of the radio signal can be controlled by controlling the electrical power to be supplied from a power supply circuit 46 to the transmitter 24. Thus, a main body communication section for receiving a radio signal and transmitting a radio signal as required is constituted by the modulator 22, transmitter 24, branching filter 26, antenna 28, receiver 32 and demodulator 34.

Upon receipt of an output command signal transmitted from the foot switch 12, the main body control unit 45 applies drive signals (high frequency voltage signals), through an oscillating/driving circuit 48, to a vibrating element, not shown, which is incorporated in a handpiece 50, and converts the drive signals into mechanical vibration. Thus, the vibrating element generates ultrasonic vibration. An operator can set an output intensity of the ultrasonic vibration (vibration intensity of the vibrating element) at any level by operating an output setting switch 52 that serves as an output setting part of the apparatus main body 44.

It is to be understood that, in the present embodiment, the vibrating element constantly vibrates with the maximum output intensity irrespective of the setting by an operator while the first pedal 18a is being depressed, and vibrates at an output intensity set by an operator while the second pedal 18b is being depressed. Thus, an output producing section for the apparatus main body 44 is constituted by the main body control unit 45, the oscillating/driving circuit 48 and the handpiece 50.

Figure 2B:
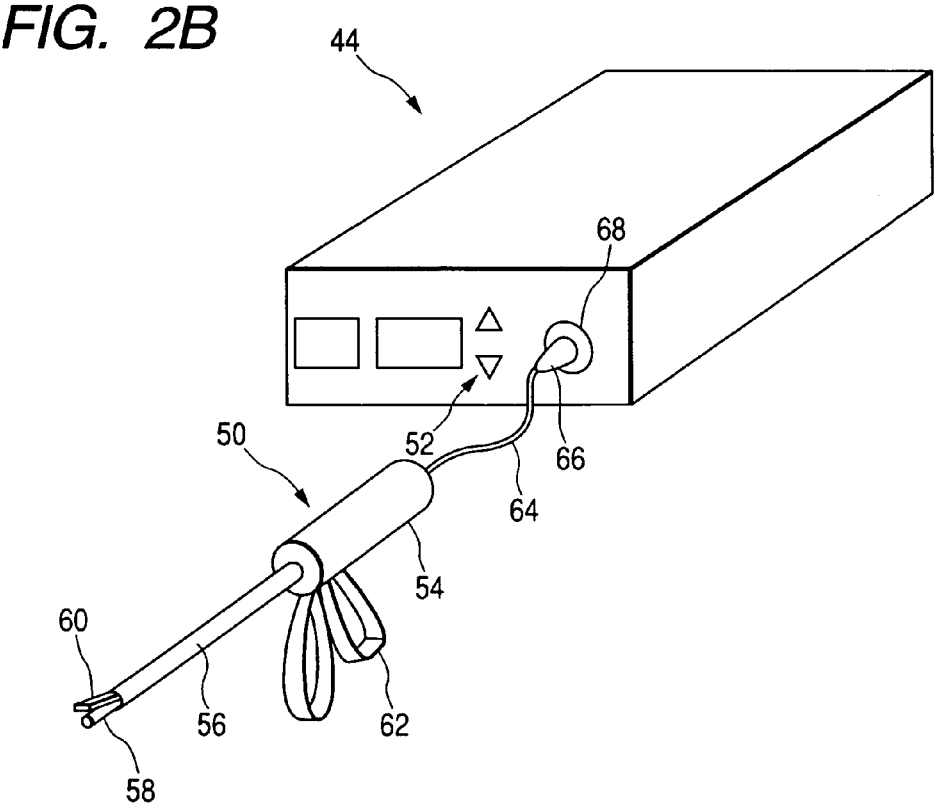
FIG. 2B is a perspective view showing an appearance of the apparatus main body of FIG. 2A.

As shown in FIG. 2B, the handpiece 50 comprises a gripper 54 to be gripped by an operator. A sheath 56 is connected to a front end of the gripper 54. A probe 58 is inserted through the sheath 56. A front end of the probe 58 is projected from the sheath 56, and a rear end of the probe 58 is connected to the vibrating element which is disposed in the gripper 54. A jaw 60 is disposed at a tip of the sheath 56 so as to hold an object to be treated, cooperating with a tip of the probe 58. The jaw 60 is configured such that it is in contact with or apart from the probe 58 interlocking with an opening/closing operation of a handle 62 which is disposed at the gripper 54.

Further, a cable 64 is extended from a rear end of the gripper 54 to supply the drive signals to the vibrating element. The cable 64 is connected to a connector 66 which is further connected to a corresponding connector 68 on a front face of a main unit of the apparatus main body 44. The antenna 28 is disposed at a rear of the main unit of the apparatus main body 44.

Figure 3:
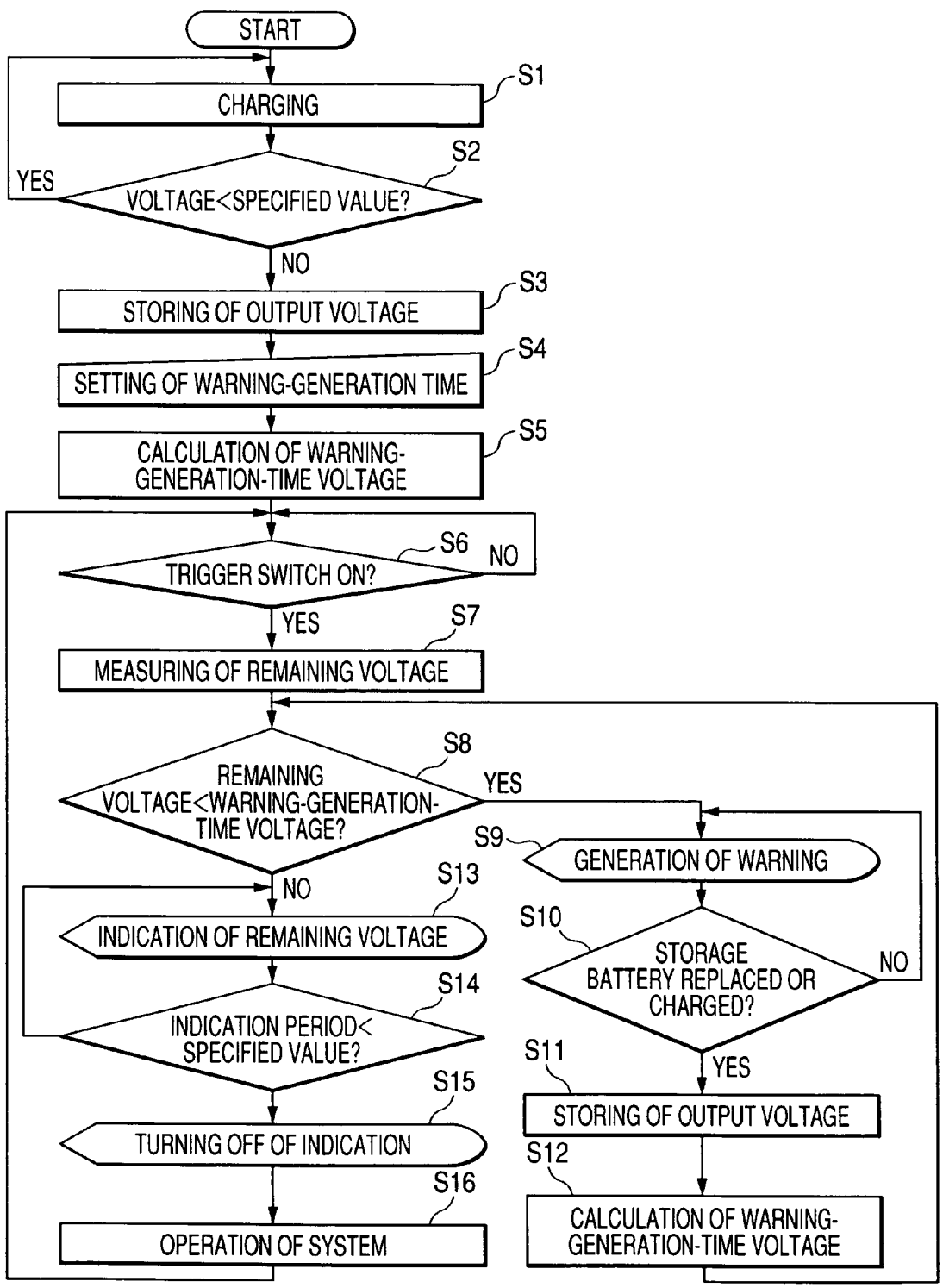
FIG. 3 is a flow diagram for explaining an operation of the ultrasonic surgical system according to the first embodiment of the present invention.

Hereinafter is described an operation of the ultrasonic surgical system according to the present embodiment, with reference to the flow diagram shown in FIG. 3. In using the ultrasonic surgical system, a power source of the apparatus main body 44 is turned on first, and at the same time a power source 16 of the foot switch 12 is also turned on to start up the foot switch 12.

At step S1, the storage battery 14 is charged using a charger (not shown). A charging rate of the storage battery 14 can be obtained based on the voltage of the storage battery 14. At step S2, a determination is made as to whether or not the voltage of the storage battery 14 has reached a specified value. If the voltage is determined, at step S2, as not having reached the specified value, control returns to step S1 to continue charging. If contrarily the voltage is detected, at step S2, to be equal to or more than the specified value, it is determined that the charging of the storage battery 14 has been completed, and the operation process proceeds to step S3.

At step S3, the control unit 20 stores an output voltage of the storage battery 14 in the internal memory. The control unit 20 calculates a remaining power suppliable time of the storage battery 14 based on a remaining voltage of the storage battery 14, referring to the output voltage stored in the memory, and the relation between the output voltage of the storage battery 14 and the power suppliable time of the storage battery 14 fully charged, which has been stored in the memory in advance. The remaining voltage is indicated on the display 40 of the foot switch 12 for a predetermined period of time.

At step S4, a warning-generation time is set by a setting switch 42a of the foot switch 12. The warning-generation time is determined by an operator based on, for example, an expected time of use in a circumstance (e.g., a hospital) where the foot switch 12 is used. At step S5, the control unit 20 calculates a remaining voltage (warning-generation-time voltage) corresponding to the preset warning-generation time. Subsequently, the operation process proceeds to step S6 where a manipulation of the trigger switch 38 is awaited.

An electrical power consumed at step S6 is minimized at a level required for detecting a manipulation of the trigger switch 38.

At step S6, if a manipulation is detected to have been performed on the trigger switch 38, the operation process proceeds to step S7 where a remaining voltage of the storage battery 14 is measured by the voltage measuring part 36. Then, at step S8, the control unit 20 compares the remaining voltage with the warning-generation-time voltage.

At step S8, if a remaining voltage is recognized to be lower than the warning-generation-time voltage, the operation process proceeds to step S9 to generate a warning by sounding the buzzer 43. Thereafter, at step S10, replacement or charging of the storage battery 14 is awaited. When the control unit 20 detects replacement or charging of the storage battery 14, the process proceeds to step S11 where the control unit 20 stores an output voltage, i.e. the maximum output voltage of the storage battery 14 at this time. Then, the operation process proceeds to step S12 to calculate a warning-generation-time voltage through the same processings as those at step S5. After completing the processings at step S12, the process returns to step S8.

Contrarily, if a remaining voltage is detected to be equal to or higher than the warning-generation-time voltage, the operation process proceeds to step S13 where the remaining voltage of the storage battery 14 is indicated on the display 40 of the foot switch 12. This indication continues for a predetermined period of time by a loop operation at step S14. After lapse of the predetermined time, the indication of the remaining voltage is turned off at step S15.

Then, at step S16, the ultrasonic surgical system is put into operation. Specifically, an operator may depress, by foot, the first pedal 18a or the second pedal 18b of the foot switch 12 while operating the handpiece 50. More specifically, the operator may operate the handle 62 to hold tissues to be treated between the jaw 60 and the probe 58, and depress the first pedal 18a or the second pedal 18b. The depression may allow a transmission of an output command signal from the foot switch 12, in the form of a radio wave. When this output command signal is received by the apparatus main body 44, the vibrating element in the handpiece 50 vibrates to effect ultrasonic treatment for the tissues. It is to be understood that when the first pedal 18a is depressed, ultrasonic vibration is outputted from the handpiece 50 with the maximum output intensity, and when the second pedal 18b is depressed, ultrasonic vibration of a preset output intensity is outputted from the handpiece 50. Thus, the tissues to be treated held between the jaw 60 and the probe 58 can be coagulated and incised by the effect of the ultrasonic vibration.

As will be apparent from the description provided above, the ultrasonic surgical system according to the present embodiment has the following effects.

An indication of a remaining voltage of the storage battery 14 can be provided on the display 40 by manipulating the trigger switch 38 of the foot switch 12. Since a remaining voltage of the storage battery 14 is in substantially a linear relationship with a remaining time during which power can be supplied to the output command signal generating section from the storage battery 14, the operator can estimate from the remaining voltage a remaining power suppliable time, i.e. a remaining usable time of the foot switch 12. Accordingly, an operator can take measures, such as by replacing or charging the storage battery 14 on the basis of the remaining voltage. Additionally, the foot switch 12 can be prevented from being disabled during surgery due to voltage deterioration resulting from discharge of the storage battery 14, by an operator's check of a remaining usable time of the foot switch 12 before starting surgery. Thus, no auxiliary battery or the like is required to be provided to the foot switch 12.

In this way, according to the present embodiment, a small-size foot switch of excellent layout freedom and portability can be provided.

In the present embodiment, although the buzzer 43 is used as a warning generator to give a sonorous warning, other manners of warning, such as an optical or vibratory warning may be employed. Alternatively, any combination of sonorous, optical and vibratory warnings may be employed.

A second embodiment of the present invention is described hereunder. A circuitry of a foot switch in an ultrasonic surgical system according to the second embodiment is the same as the circuitry, shown in FIG. 1, of the foot switch 12 according to the first embodiment. However, the second embodiment is different from the first embodiment in that, utilizing the substantially linear relation between a remaining power suppliable time and a remaining voltage, the control unit 20 of the foot switch has a function of calculating a remaining power suppliable time based on a remaining voltage of the storage battery 14, and that the calculated remaining time is indicated on the display 40 instead of the remaining voltage.

With the ultrasonic surgical system of the present embodiment, since a remaining power suppliable time is indicated on the display 40 when the trigger switch 38 is manipulated, and thereby an operator can know the remaining usable time of the foot switch, an advantage of more excellent usability can be obtained.

Figure 4:
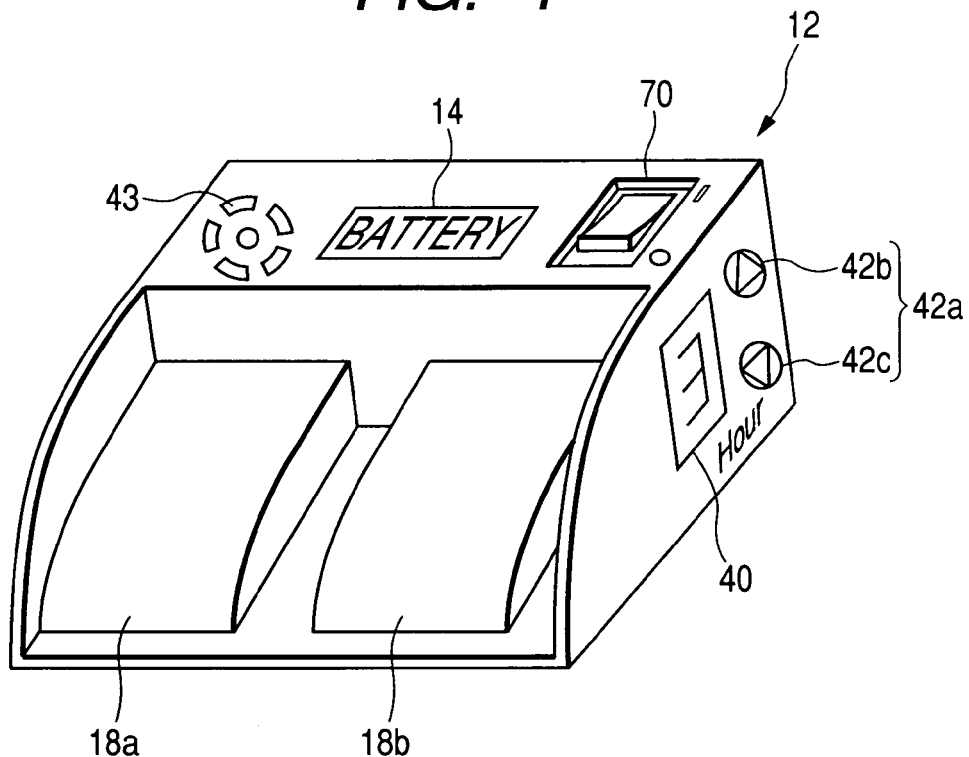
FIG. 4 is a perspective view showing an appearance of a foot switch in an ultrasonic surgical system according to a third embodiment of the present invention.

FIG. 4 shows an appearance of a foot switch in an ultrasonic surgical system according to a third embodiment of the present invention. As shown in FIG. 4, no trigger switch 38 (see FIG. 1B) is provided to the foot switch of the present embodiment. A power switch 70 serves also as the trigger switch 38.

In using the ultrasonic surgical system of the present embodiment, upon startup of the foot switch 12 by turning on the power switch 70, a remaining power suppliable time is indicated on the display 40. However, if a warning-generation time is yet to be set, the system may flash, for example, a warning lamp, not shown, to encourage an operator to set a warning-generation time.

According to the ultrasonic surgical system of the present embodiment, usability is further improved because a remaining usable time of a foot switch is always indicated on the display 40 when the power switch 70 is turned on.

Figure 5:
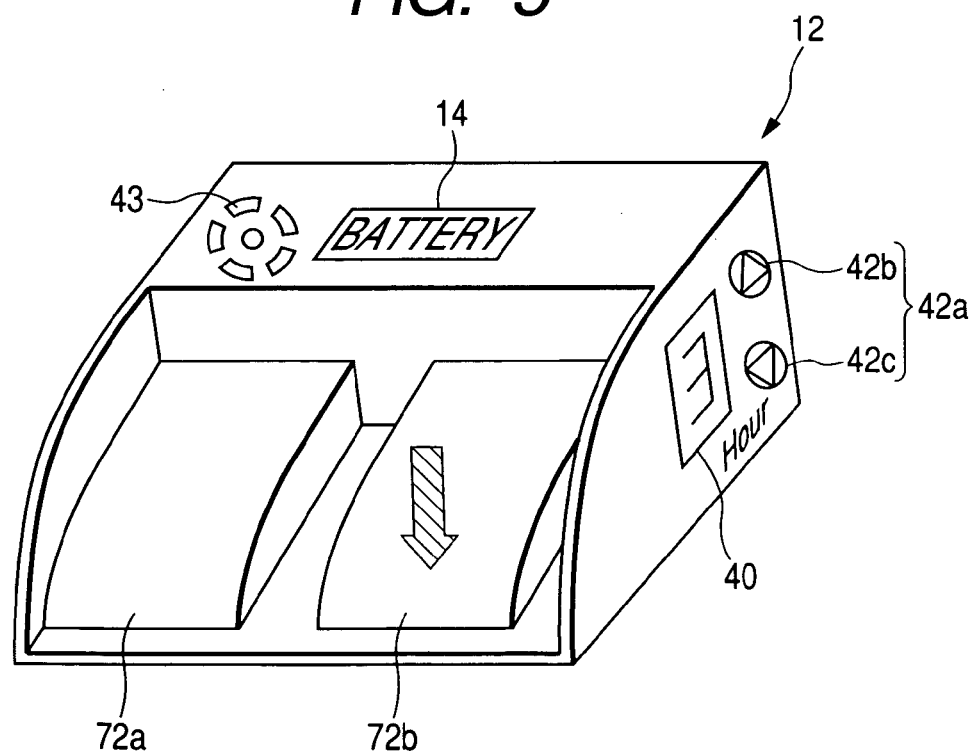
FIG. 5 is a perspective view showing an appearance of a foot switch in an ultrasonic surgical system according to a fourth embodiment of the present invention.

FIG. 5 shows an appearance of a foot switch in an ultrasonic surgical system according to a fourth embodiment of the present invention. As shown in FIG. 5, in the foot switch 12 of the present embodiment, a first pedal 72a and a second pedal 72b serve also as both the power switch 16 (see FIG. 1B) and the trigger switch 38 (see FIG. 1B). Further, the setting switch 42a also serve as the power switch 16 (see FIG. 1B).

In the ultrasonic surgical system according to the present embodiment, the foot switch 12 may start up when either of the first and second pedals 72a, 72b is depressed for indication of a remaining usable time on the display 40 and for transmission of an output command signal. However, if a warning-generation time is yet to be set, a warning lamp, not shown, may be flashed, for example, to encourage an operator to set a warning-generation time. The foot switch 12 may also start up by the depression of the setting switch 42a.

In the ultrasonic surgical system according to the present embodiment, a remaining usable time of a foot switch is automatically indicated on the display 40 every time the first or second pedal 72a, 72b is depressed, thereby providing an advantage of more improved usability.

Figure 6:
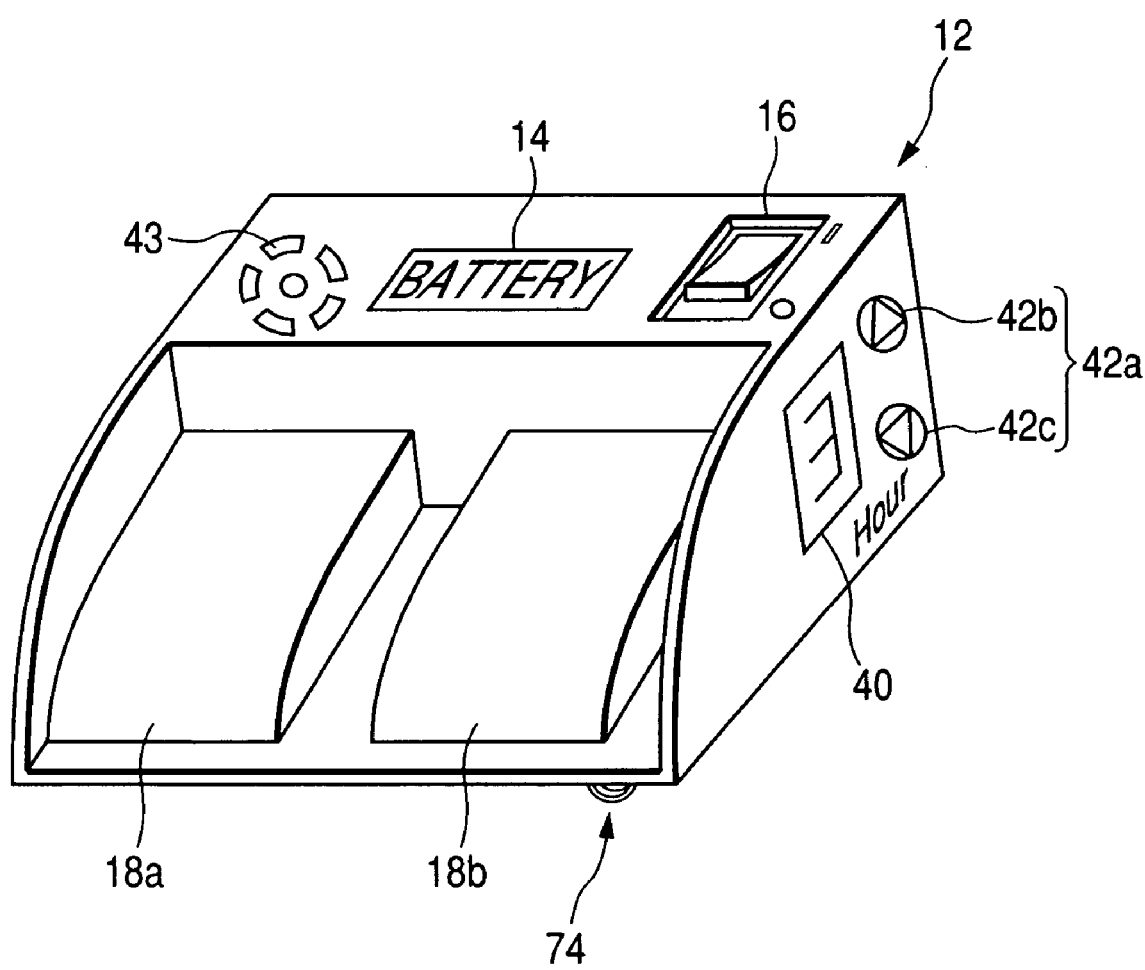
FIG. 6 is a perspective view showing an appearance of a foot switch in an ultrasonic surgical system according to a fifth embodiment of the present invention.

FIG. 6 shows an appearance of a foot switch in an ultrasonic surgical system according to a fifth embodiment of the present invention. As shown in FIG. 6, the foot switch 12 of the present embodiment comprises a movement detection switch 74. The movement detection switch 74 is a switch retractably disposed at a bottom surface of the foot switch 12, and is configured to be turned off when retracted, and to be turned on when projected. Specifically, when the foot switch 12 is placed such as on a floor, the movement detection switch 74 is in a retracted state so as to be turned off, and when the foot switch 12 is lifted up for transfer, the movement detection switch 74 is in a projected state so as to be turned on.

In the present embodiment, when the foot switch 12 is lifted up after use or during rearrangement of layout, the movement detection switch 74 is turned on to indicate on the display 40 a remaining usable time of the foot switch.

Thus, in the ultrasonic surgical system according the present embodiment, since a remaining usable time is indicated when confirmation thereof is required, i.e., for example, after use or during rearrangement of layout of the foot switch 12, usability is more improved.

It is to be understood that, instead of the movement detection switch 74, a tilt sensor or a gyro sensor may be used as means for detecting movement of the foot switch 12.

Figure 7A:
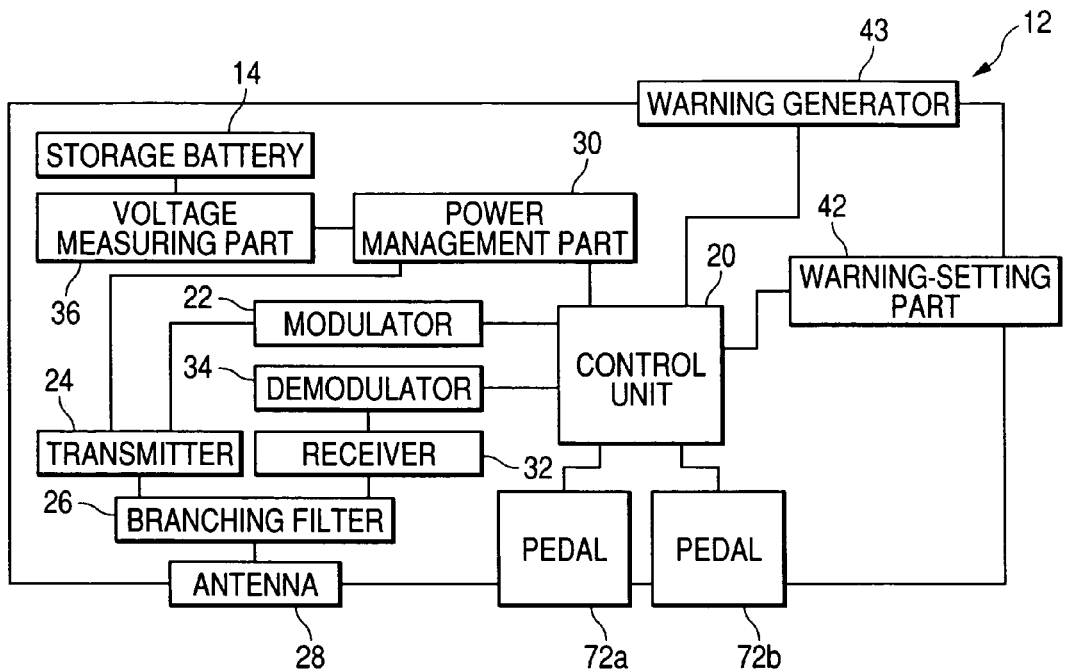
FIG. 7A is a block diagram showing a circuitry of a foot switch in an ultrasonic surgical system according to a sixth embodiment of the present invention.
Figure 7B:
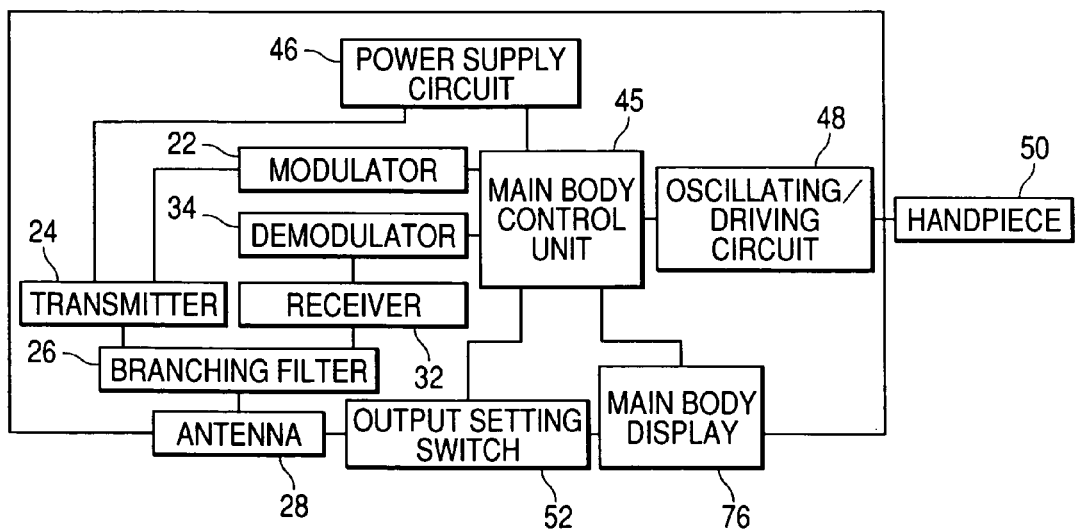
FIG. 7B is a block diagram showing a circuitry of an apparatus main body in the ultrasonic surgical system according to the sixth embodiment of the present invention.

FIG. 7A shows a circuitry of the foot switch 12 in an ultrasonic surgical system according to a sixth embodiment of the present invention, and FIG. 7B shows a circuitry of the apparatus main body 44 in the ultrasonic surgical system according to the present embodiment.

As shown in these figures, in the present embodiment, the foot switch 12 is not provided with the display 40, but a main body display 76 is provided to the apparatus main body 44. In the ultrasonic surgical system according to the present embodiment, when either of the first and second pedals 72a, 72b of the foot switch 12 is depressed, the control unit 20 calculates a remaining usable time of the foot switch 12. The calculated remaining usable time is transmitted to the apparatus main body 44 together with an output command signal through the modulator 22, transmitter 24, branching filter 26 and antenna 28. The transmitted remaining usable time is then inputted to the main body control unit 45 through the antenna 28, branching filter 26, receiver 32 and demodulator 34 of the apparatus main body 44. The main body control unit 45 transmits the inputted remaining usable time to the main body display 76 which is analogous to the display 40 (see FIG. 1B) of the foot switch 12. Thus, the remaining usable time is indicated on the main body display 76.

In the ultrasonic surgical system according to the present embodiment, upon depression of either of the first and second pedals 72a, 72b of the foot switch 12, a remaining usable time of the foot switch is indicated on the main body display. The present embodiment is advantageous in a circumstance where obtaining a good sight of the display 40 of the foot switch 12 is difficult.

Although the present invention has been described by way of several ultrasonic surgical systems, the present invention is applicable to any system employing a wireless foot switch. For example, the present embodiment is applicable to a system which includes an imaging device such as a flexible endoscope or a rigid endoscope, and performs freezing, recording, GAIN control, magnification control, rotation or the like on picture images by use of the foot switch. In this case, the remaining voltage or remaining power suppliable time can be indicated together with an image under observation.

What is claimed is:

1. A foot switch comprising:
   a pedal;
   an output command signal generating section transmitting, when said pedal is operated, an output command signal to an apparatus main body having a function of producing active output;
   a storage battery supplying electrical power to said output command signal generating section;
   a condition-detecting section detecting a remaining capacity of said storage battery;
   a notifying section making notification of an amount corresponding to said remaining capacity detected by said condition-detecting section; and
   a movement detection switch for detecting whether or not said foot switch is moved, said notifying section making said notification when said movement detection switch detects that said foot switch is moved.

2. The foot switch according to claim 1, wherein said output command signal generating section includes a radio communication section radio-transmitting said output command signal.

3. The foot switch according to claim 1, wherein said condition-detecting section detects said remaining capacity of said storage battery on the basis of a remaining voltage of said storage battery.

4. The foot switch according to claim 1, wherein said notifying section makes notification of a remaining voltage of said storage battery.

5. The foot switch according to claim 1 further comprising a calculating section calculating, on the basis of said remaining capacity detected by said condition-detecting section, a remaining time during which said storage battery can supply electric poser to said output command signal generating section, said notifying section making notifying of said remaining time calculated by said calculating section.

6. The foot switch according to claim 1 further comprising a trigger switch, said notifying section determining said notification amount when said trigger switch is operated.

7. The foot switch according to claim 1 further comprising an activation switch for activating said foot switch, said notifying section making said notification when said activation switch is operated.

8. The foot switch according to claim 1, wherein said notifying section makes said notification when said pedal is operated.

9. An output system including a foot switch and an apparatus main body having a function of producing active output,
   said foot switch comprising:
   a pedal;
   an output command signal generating section transmitting an output command signal to said apparatus main body when said pedal is operated;
   a storage battery supplying electrical power to said output command signal generating section;
   a condition-detecting section detecting a remaining capacity of said storage battery;
   a notifying section making notification of an amount corresponding to said remaining capacity detected by said condition-detecting section; and
   a movement detection switch for detecting whether or not said foot switch is moved, wherein said notifying section makes said notification when said movement detection switch detects that said foot switch is moved;

said apparatus main body comprising:

an output producing section producing active output upon receiving said output command signal transmitted from said foot switch.

10. The output system according to claim 9, wherein said output command signal generating section of said foot switch includes a communication section radio-transmitting said output command signal, and said apparatus main body includes a main body communication section receiving said output command signal radio-transmitted from said foot switch.

11. The output system according to claim 9, wherein said output producing section includes an ultrasonic vibrating element.

12. An output system including a foot switch and an apparatus main body having a function of producing active output, said foot switch comprising:

a pedal;

an output command signal generating section transmitting an output command signal to said apparatus main body when said pedal is operated;

a storage battery supplying electrical power to said output command signal generating section;

a condition-detecting section detecting a remaining capacity of said storage battery; and a movement detection switch for detecting whether or not said foot switch is moved;

said output command signal generating section including a communication section transmitting said output command signal, said remaining capacity detected by said condition-detecting section to said apparatus main body and a notification when said movement detection switch detects that said foot switch is moved;

said apparatus main body comprising:

a main body communication section receiving said output command signal and said remaining capacity transmitted from said foot switch;

an output producing section producing active output when said main body communication section receives said output command signal transmitted from said foot switch; and a main body notifying section making notification of an amount corresponding to said remaining capacity when said main body communication section receives said remaining capacity transmitted from said foot switch.

13. The output system according to claim 12, wherein said output producing section includes an ultrasonic vibrating element.

* * * * *